(12) United States Patent
Buchnick et al.

(10) Patent No.: US 8,031,075 B2
(45) Date of Patent: Oct. 4, 2011

(54) WEARABLE DEVICE FOR ADAPTIVELY RECORDING SIGNALS

(75) Inventors: Judy Buchnick, Givat Shmuel (IL); Uri Shir, Ra'Anana (IL); Itzhak Pomerantz, Kfar Saba (IL)

(73) Assignee: Sandisk IL Ltd., Kfar Saba (IL)

( * ) Notice: Subject to any disclaimer, the term of this patent is extended or adjusted under 35 U.S.C. 154(b) by 173 days.

(21) Appl. No.: 12/250,032

(22) Filed: Oct. 13, 2008

(65) Prior Publication Data

US 2010/0090834 A1 Apr. 15, 2010

(51) Int. Cl.
*G08B 23/00* (2006.01)
(52) U.S. Cl. .......................... 340/573.1; 701/35; 368/204
(58) Field of Classification Search ............... 340/573.1, 340/573.4, 539.1, 539.13, 539.16; 368/204; 701/35
See application file for complete search history.

(56) References Cited

U.S. PATENT DOCUMENTS

| | | | |
|---|---|---|---|
| 3,855,416 A | 12/1974 | Fuller | |
| 3,855,417 A | 12/1974 | Fuller | |
| 3,855,418 A | 12/1974 | Fuller | |
| 3,971,034 A | 7/1976 | Bell, Jr. et al. | |
| 4,093,821 A | 6/1978 | Williamson | |
| 4,142,067 A | 2/1979 | Williamson | |
| 5,495,357 A * | 2/1996 | Osterhout | 398/107 |
| 6,072,392 A * | 6/2000 | Henderson et al. | 340/539.15 |
| 6,072,396 A * | 6/2000 | Gaukel | 340/573.4 |
| 6,405,213 B1 * | 6/2002 | Layson et al. | 340/539.1 |
| 7,453,364 B2 * | 11/2008 | Sarel et al. | 340/573.1 |
| 2004/0172290 A1 * | 9/2004 | Leven | 705/2 |
| 2004/0249634 A1 | 12/2004 | Degani et al. | |
| 2005/0108775 A1 | 5/2005 | Bachar et al. | |
| 2005/0184870 A1 * | 8/2005 | Galperin et al. | 340/568.2 |

OTHER PUBLICATIONS

Masubuchi, Hideyuki et al., "An Acoustic Abnormal Detection System", Dept. of Electrical Eng., Hosei University, IEEE International Workshop on Robot and Human Communication, 1993, 6 pages.
Xie, Qiaobing et al., "Automatic Assessment of Infants' Levels-of-Distress from the Cry Signals", IEEE Transactions on Speech and Audio Processing, Jul. 1996, 13 pages, vol. 4, No. 4.
Baeck, H.E. et al., "A Bayesian Classifier for Baby's Cry in Pain and Non-Pain Contexts", Proceedings of the 25th Annual International Conference of the IEEE EMBS, Cancun, Mexico, Sep. 17-21, 2003, 3 pages.

* cited by examiner

*Primary Examiner* — George Bugg
*Assistant Examiner* — Edny Labbees
(74) *Attorney, Agent, or Firm* — Toler Law Group

(57) ABSTRACT

A condition of a subject is monitored by a wearable recording unit that adaptively records various signals associated with the condition of the subject. The various signals are recorded by the wearable recording unit using a recording plan that is contextually adaptively updated to the monitored subject from one recording session to another based on the result of the analysis of previous recording sessions.

23 Claims, 8 Drawing Sheets

WEARABLE DEVICE FOR ADAPTIVELY RECORDING SIGNALS

FIELD OF THE INVENTION

The present invention generally relates to monitoring systems and more specifically to a wearable monitoring device capable of adaptively recording signals.

BACKGROUND

Monitoring conditions of or near subjects such as human beings, animals, and machines is often used to track processes, detect abnormalities, log events and create alerts. For example, working mothers of infants and young children oftentimes leave their children for long time periods in the care of others. Experience shows that, at times, care givers abuse, neglect young children and infants in their care or expose these children to harmful conditions. For example, there are reported cases where infants were left unattended in a car in a hot day with all the car's windows rolled up. Therefore, parents are often concerned about the wellbeing of their children when they are at work.

One solution to mitigate the parents' stress and anxiety involves installing a hidden video camera in an attempt to monitor the environment of the child and its care giver (e.g., nanny or babysitter). Various camera-based systems are known in the field as "NannyCam" systems. NannyCam systems are expensive and, once positioned, the hidden cameras are stationary. Therefore, this type of solution is efficient only if the monitored subject (e.g., an infant) remains in the Field of View ("FOV") of the camera. However, the care giver may sometimes take the child or infant from a monitored room to an unmonitored room, or to a nearby park, where the camera is useless.

Another solution involves monitoring sounds. However, sound monitoring systems leave the decision regarding the condition of the infant to the parents. Not knowing exactly what the parents should expect, they may overlook meaningful or critical information related to mistreatment of their child. Other solutions involve attempting to monitor child activity or to monitor the location of a child.

Such solutions are not user friendly and provide raw data which has to then be analyzed, if possible. These solutions tend to produce excessive amounts of irrelevant data which at times may mask important data that cannot be easily ascertained.

There is therefore a need to provide more efficient monitoring of subjects. There is a need to make this monitoring more useful in providing more relevant and easy to process data.

SUMMARY

In view of the foregoing, it would be beneficial to have a monitoring device to monitor various signals relating to the condition of or near a subject but to record only relevant signals according to a recording plan. There is also an advantage in automatically adapting the recording plan of the recording device according to previously recorded signals.

Preferably, a wearable recording unit would adaptively record various signals that pertain to the physiological condition of a subject by using a recording plan that is automatically updated from one recording session to another. The adaptation of such a recording plan would be based on the analysis of previously recorded signals. Various embodiments are designed to implement such capability, examples of which are provided herein. The following exemplary embodiments and aspects thereof are described and illustrated in conjunction with systems, tools, and methods, which are meant to be exemplary and illustrative but not limiting in scope.

A system may be provided, which includes one or more signal sensors and a wearable recording unit that is operative to record one or more signals of the signal sensors according to a recording plan. The recorded signals may represent one or more conditions such as physical and physiological conditions as well as events of abnormality in such conditions. The physical or physiological conditions may include one or more of movement, force and pressure, as well as, acoustical, thermal, electromagnetic and electrical phenomena.

The signal sensors may include a microphone to monitor sounds; a movement detector to detect sudden or abnormal movements, a strain gauge to detect stress force, a pressure sensor, a temperature sensor, and an ultra-violet sensor to monitor ultra-violet radiation to which the subject is exposed. The movement detector may include one or more accelerometers that are arranged in the wearable recording unit in a way that spatial movements can be identified. One or more of the signal sensors may be embedded in the wearable recording unit.

The system may further include a docking station for receiving the recording unit. The docking station may include an analyzer for analyzing recorded signals, and a controller for adapting the recording plan for the wearable recording unit based on such analysis, based on user input, or based on both. The wearable recording unit is configured to record signals in accordance with the adapted recording plan. Each of the recording plan and adapted recording plan is operative to set one or more of schedule, sensitivity, duration and resolution of the recording of signals.

A recording plan may include one or more recording instructions for the wearable recording unit as to which signal should be recorded and when it should be recorded. Responsive to receiving a recording instruction under a plan or adapted recording plan the wearable recording unit may record a sensor's signal (i) if the signal matches a predefined pattern, and/or (ii) if the value or average value of the signal exceeds a predetermined threshold value for a predetermined duration or regardless of such duration, and/or (iii) if the time characteristics, the frequency characteristics, or both characteristics of the signal match predefined characteristics The wearable recording unit may time stamp selected recordings of signals to facilitate logging and retrieval of recorded data, and to facilitate various types of signal calculations, assessments, and/or evaluations. The wearable recording unit may be initialized with a default recording plan either by a user of the wearable recording unit (e.g., by a parent of a monitored infant), or by the controller of the docking station. The wearable recording unit and the docking station may communicate via a Universal Serial Bus ("USB") interface. The wearable recording unit may include a flash memory device for holding recorded signals and recording instructions associated with recording plans. The docking station may further include a user interface for providing the user input to the controller, and for outputting information regarding recorded signals and recording plans.

A wearable recording unit is also provided for adaptively recording signals that pertain to the condition of a subject. The wearable recording unit includes one or more signal sensors; a sensors' interface for translating the electrical signals of the signal sensors into corresponding digital data; an attachment for attaching the wearable recording unit to or near the subject; a memory unit for holding recording instructions associated with recording plans, and signals recorded according to enforced recording instructions. The memory unit may be, or it may include, a flash memory device.

The wearable recording unit also includes a recording controller. The recording controller may be configured (i) to receive a recording instruction based on a recording plan and to record sensor signals in the memory unit based on the recording instruction, (ii) to transfer recorded signals to a docking station for analysis, and (iii) to receive from the docking station and to enforce a recording instruction under the recording plan which is adapted in response to previously analyzed recorded signals. Each of the recording plan and adapted recording plan may be operative to set one or more of schedule, sensitivity, duration and resolution of the recording of signals.

The wearable recording unit also includes an attachment for attaching the wearable recording unit to or near the subject. The attachment may be, for example, a wrist strap. A first end of the recording unit may be affixed to a first electrical connector and a second end of the recording unit may be affixed to a first end of the wrist strap. A second end of the wrist strap may include a second electrical connector, where the first electrical connector and the second electrical connector are adapted to be functionally connected to the docking station. The first and the second electrical connectors may be provided with a locking mechanism. The first electrical connector may be, for example, a male USB connector and the second electrical connector may be, for example, a female USB connector.

A method is also provided for adaptively recording signals that pertain to the condition of a subject. The method includes recording, by a wearable recording unit, signals of one or more signal sensors by using a recording plan; analyzing, by a docking station, the recorded signals; adapting, by the docking station, the recording plan for the wearable recording unit based on such analysis, based on user input, or based on both; and operating the wearable recording unit to record signals in accordance with the adapted recording plan by enforcing on the wearable recording unit one or more recording instructions corresponding to the used recording plan.

The method may further include, responsive to receiving a recording instruction under a plan or adapted plan, a step of recording a sensor's signal (i) if the signal matches a predefined pattern, (ii) if the value or average value of the signal exceeds a predetermined threshold value for a predetermined duration or regardless of such duration, or (iii) if the time characteristics, the frequency characteristics, or both characteristics, of the signal match predefined characteristics. The method may further include a step of setting one or more of schedule, sensitivity, duration and resolution of the recording of signals. The method may further include storing one or more recording instructions in the wearable recording unit to use a basic recording mode, or to change a recording mode, or to operate at a specific recording mode for a specified time window.

In addition to the exemplary aspects and embodiments described above, further aspects and embodiments will become apparent by reference to the figures and by study of the following detailed description.

BRIEF DESCRIPTION OF THE DRAWINGS

Exemplary embodiments are illustrated in referenced figures. It is intended that the embodiments disclosed herein are illustrative rather than restrictive. The disclosure, however, may better be understood with reference to the following detailed description when read with the accompanying figures, in which.

Figure 1:
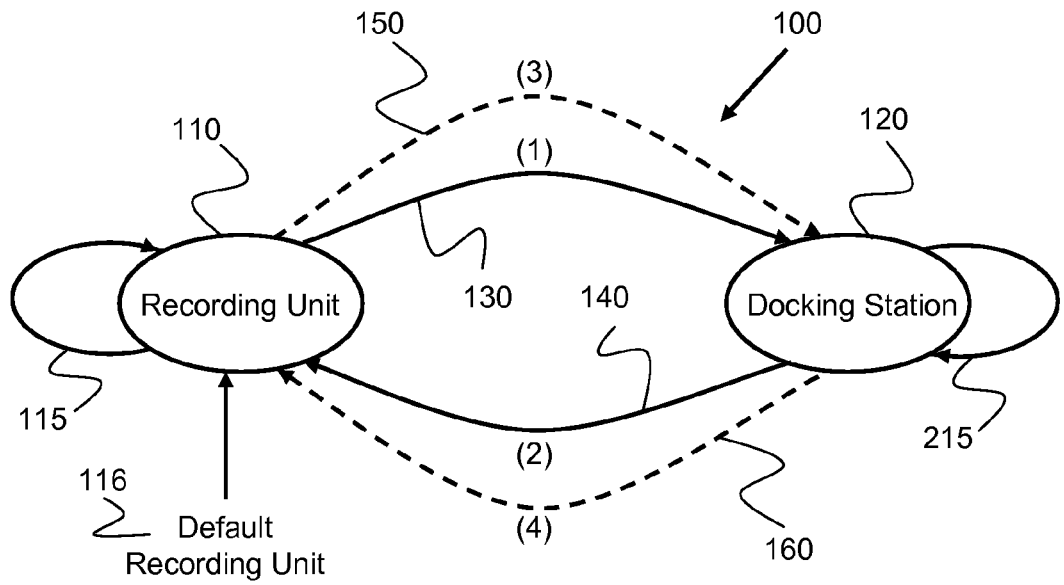
FIG. 1 is a state diagram of a recording system according to an example embodiment.

It will be appreciated that for simplicity and clarity of illustration, elements shown in the figures are not necessarily drawn to scale. Further, where considered appropriate, reference numerals may be repeated among the figures to indicate like, corresponding or analogous elements.

DETAILED DESCRIPTION

The description that follows provides various details of example embodiments. However, this description is not intended to limit the scope of the claims but instead to explain various principles of the invention and the manner of practicing it.

FIG. 1 is a state diagram 100 associated with the operation of a monitoring system in accordance with the present disclosure. State diagram 100 illustrates an interaction between recording unit 110 and docking station 120. In general, recording unit 110 records signals based on a recording plan and docking station 120 analyzes the recorded signals. Based on the analysis results docking station 120 adapts, updates or revises the recording plan for recording unit 110.

If it is required or desired to monitor the wellbeing of a subject, which may be, for example, a person, an infant, a child, an elder, a disabled person or an animal (e.g., a dog or a cat), recording unit 110 is attached to the subject by using an attachment device such as a wrist strap or another tethering device. When wearable recording unit 110 is attached to the infant it is operating in a "recording mode". While in the recording mode recording unit 110 continually, occasionally, or intermittently, records one or more signals (the recording of signals being symbolically shown as an arrow 115) pertaining to the condition of the infant according to a recording plan. Recording unit 110 may initially use some default recording plan 116. Default recording plan 116 may be provided to recording unit 110 either at the time of manufacturing of recording unit 110 or by the user of recording unit 110 (e.g., a concerned parent of the infant), for example through docking station 120. If it is required or desired to analyze the recorded signals and to update the recording plan, recording unit 110 is detached from the infant and connected to docking station 120. When wearable recording unit 110 is connected to docking station 120 it is operating in a "docking mode". While in the docking mode wearable recording unit 110 transfers the recorded signals (shown at 130) to docking station 120. Then, docking station 120 analyzes the recorded signals (the analysis being symbolically shown as an arrow 125) to identify whether any recorded signal includes irregularities or abnormalities. The analysis of recorded signals may include comparing signals to predetermined patterns of interest and/or to other criteria.

If docking station 120 identifies irregularities or abnormalities in the analyzed signals docking station 120 uses these irregularities or abnormalities to adaptively update, revise, replace, or regenerate the recording plan for recording unit 110. "Adaptively" means that each time docking station 120 receives signals associated with a particular subject, the recording plans generated by docking station 120 tend to converge to (i.e., to zoom in on) potentially alarming conditions. Therefore, it may be said, or docking station 120 may be thought of as, adapting recording plans to the monitored subject. Because an irregularity/abnormality is associated with some context (e.g., the subject was slammed on his face), "adaptively" is equivalent to saying that docking station 120 contextually adapts the recording plans to the monitored subject.

Docking station 120, then, transfers the updated, revised, replaced, or regenerated recording plan (shown at 140) to recording unit 110. Analog signals are sampled and samples are digitized and recorded. In the context of the present disclosure "zooming in on a potentially alarming condition", or "zooming in on a condition that can trigger an alarm" means enhancing the sampling process (i.e., making the sampling process more sensitive) during a time frame in which the alarming condition is likely to reoccur. The sampling process may be enhanced by using a higher sampling rate, or by using a higher resolution (i.e., in bits per sample), or by both using a higher sampling rate and a higher resolution within the intended time frame.

Recording unit 110 is then reattached to the infant and reenters the recording mode (shown at 115); i.e., it commences a second recording session during which recording unit 110 uses substitute recording rules, other recording rules, additional recording rules, or revised recording rules, as specified by the recording plan that wearable recording unit 110 receives from docking station 120.

If it is required to analyze signals that were recorded during the second recording session (or to update the recording plan), recording unit 110 is detached again from the infant and reconnected to docking station 120. While in the docking mode for the second time wearable recording unit 110 transfers the recorded signals (shown at 150) to docking station 120. Then, docking station 120 analyzes (shown as an arrow 125) the recorded signals to identify whether any recorded signal includes irregularities or abnormalities in the analyzed signals.

If docking station 120 identifies irregularities or abnormalities in the analyzed signals docking station 120 adaptively updates, revises, replaces, or regenerates the recording plan for recording unit 110. Docking station 120, then, transfers the updated recording plan (shown at 160) to recording unit 110. Recording unit 110 may then reattached again to the infant and the signals recording and recording update process may repeat as many time times as required or desired.

Figure 2:
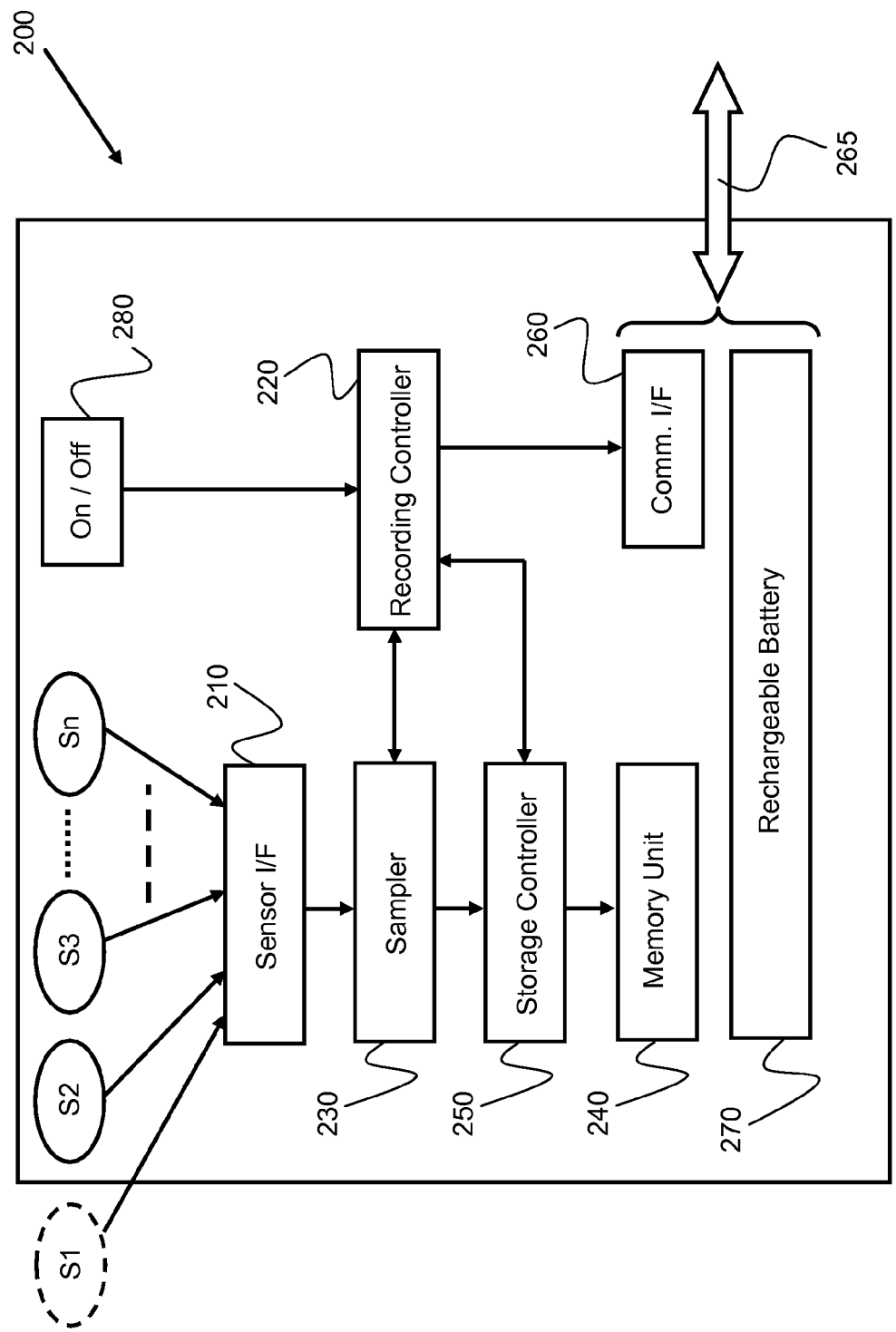
FIG. 2 is a block diagram of a recording unit according to an example embodiment.

FIG. 2 is a block diagram of a recording unit 200 according to an example embodiment. Recording unit 200 includes n signal sensors S1, S2, S3, . . . , Sn (n may equal 1). Each of signal sensors S1 through Sn may output an electrical signal that represents physical and physiological events that are associated with a monitored subject or a monitored subject's environment. In the context of recorded signals "event" refers to a signal segment that "behaves" in an unusual, unexpected, or in an abnormal way. An "event" may refer, for example, to a signal that includes an unusual or abrupt change in the signal's amplitude or has unusual time and/or frequency characteristics. An unusual or irregular cry of an infant, a scream, a sudden environmental noise, a fast heart beat rate and a high body temperature may originate exemplary events. An "event" also refers to a series of signal segments that, collectively, may indicate a potentially alarming condition. In other words, physical and physiological events result in corresponding signal events if they are properly recorded.

Physical and physiological events may include one or more of movement, force, pressure, acoustical, thermal, electromagnetic and electrical phenomena. Sudden movement of the subject is an exemplary physical phenomenon. Background noises are an exemplary acoustical phenomenon. Abnormal heart beat and skin conductivity are exemplary electrical phenomena.

By way of example, signal sensor S2 may be a microphone that outputs an electrical signal corresponding to sounds in the environment of the monitored subject; signal sensor S3 may be a thermometer that outputs an electrical signal corresponding to the subject's body temperature; S4 may be an ultra-violet sensor for recording ultra-violet radiation to which the subject is exposed, and signal sensor Sn may be a movement detector that outputs an electrical signal corresponding to the subject's spatial movements. The movement detector may include one or more accelerometers that are arranged in recording unit 200 in a way that spatial movements of the monitored subject can be identified. Other signal sensors (e.g., signal sensors S6 and S7) may output an electrical signal corresponding to the subject's heartbeats, and an electrical signal corresponding to the subject's skin electrical conduction. Additional or other signal sensors may be used. For example, signal sensor S8 may be a strain gauge that detects stress force, and signal sensor S9 may be a pressure sensor that detects external pressure that is exerted, for example, on the recording unit. The monitored subject would usually be an infant, a young child, a disabled subject, a domestic animal, etc.

Some of signal sensors S1 through Sn may be embedded in recording unit 200 and the other sensors may be external to recording unit 200. By way of example, signal sensor S1 is external to wearable recording unit 110 and signal sensors S2 through Sn are shown embedded in recording unit 200. One of signal sensors S1 through Sn may be a movement detector that provides to recording unit 200 a signal indicative of an attempt to tamper with recording unit 200.

Sensors for monitoring the subject are available on the market. For example, VTI SCA3000-D01 (a sensor made by Toradex, Swiss) senses 3-dimensional acceleration, zenith and azimuth; MS5540B (a sensor made by Intersema Sensoric SA) senses pressure and temperature; GP2D12J0000F (a sensor made by Sharp Electronics Corporation) senses distance; SHT15 (a sensor made by Sensirion AG) senses humidity and temperature; AMN11111 (a sensor made by Panasonic) senses movements of remote objects; and AS5046 (a sensor made by Austria Microsystems AG) senses angular position.

Figure 4:
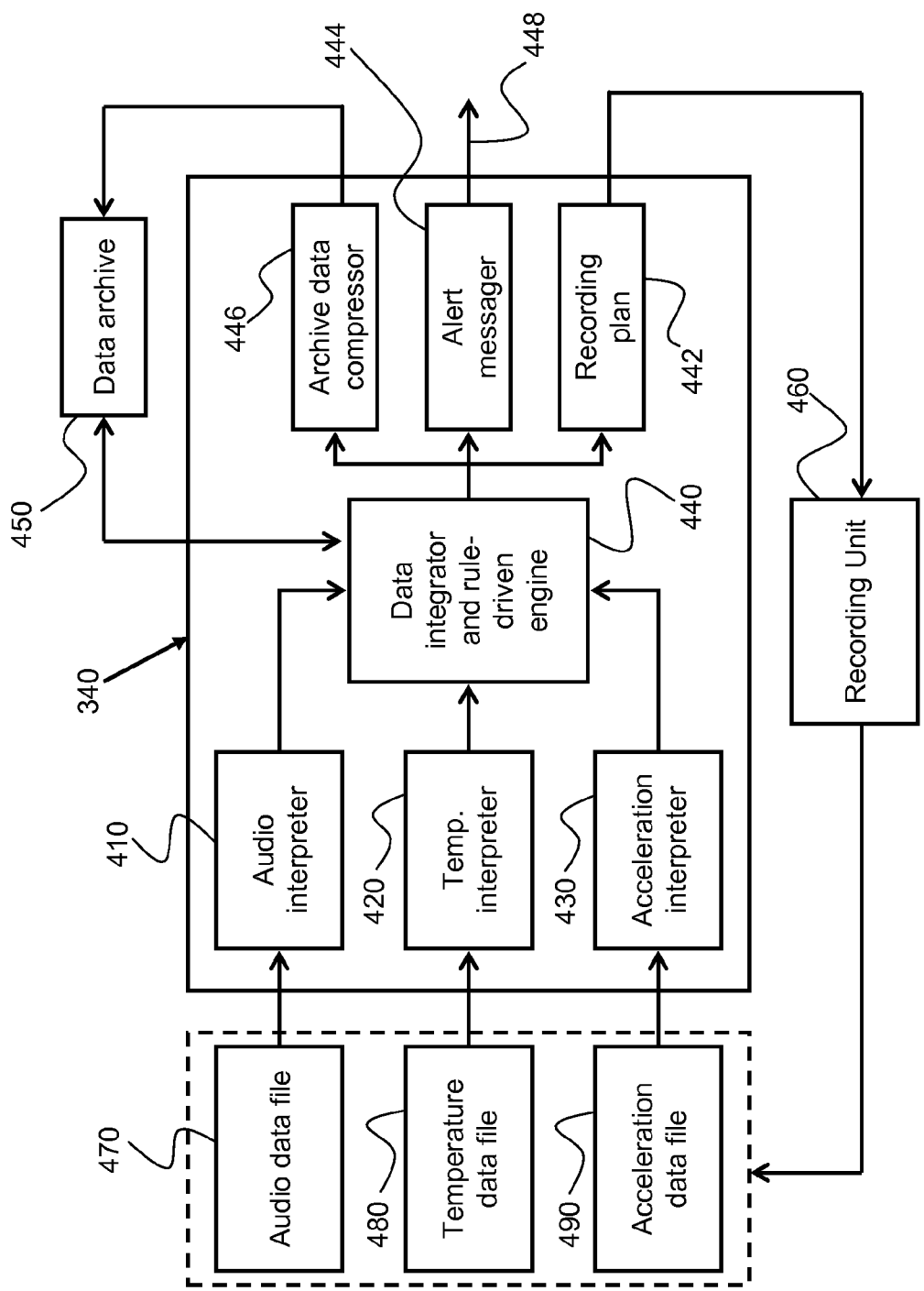
FIG. 4 is a block diagram of an analyzer according to an example embodiment.

Recording unit 200 also includes a sensor interface 210, a recording controller 220, a signal sampler 230, a memory unit 240, a storage controller 250, a communication interface 260, and a rechargeable battery 270. Sensor interface 210 translates (i.e., scales, etc.) the electrical signals of signal sensors S1 through Sn into signals that signal sampler 230 can sample and digitize. Recording controller 220 enforces recording rules according to a recording plan that it receives from a docking station via communication interface 260. In other words, recording controller 220 is instructed by the docking station as to which sensor signal should be recorded (i.e., stored in memory unit 240) and when, as is described in more detail, for example, in connection with FIGS. 5, 7, and 8, which are described below. Memory unit 240 may hold a set of one or more recording instructions that instruct recording controller 220 to record signals from one or more sensors during specific time periods. Memory unit 240 may also hold recorded signals. Storage controller 250 manages transfers of data to and from memory unit 240. Memory unit 240 may be implemented as, or it may include, a flash memory device, for example of the NAND type. Recording unit 200 also includes an attachment device for attaching wearable recording unit 110 to or near the subject whose condition is to be monitored. The attachment device may be implemented as a wrist strap, as shown in FIG. 4, which is described below.

While in the recording mode, recording controller 220 record sensors signals in memory unit 240 based on a recording plan that may be a default recording plan held in memory unit 240. While in the docking mode, recording controller 220 communicates with the docking station via communication path 265. During communication, recording controller 220 transfers recorded signals to the docking station for analysis and receives therefrom a recording instruction based on a recording plan which is adapted in response to previously recorded signals.

Recording unit 200 may include an "on/off" depressible switch 280 to allow a user of recording unit 200 (e.g., a parent of a child) to switch recording unit 200 on and off. The user may switch recording unit 200 "on" after recording unit 200 is attached to the subject. The user may switch recording unit 200 "off" when wearable recording unit 110 is detached from the subject, and again to "on" when s/he reattaches recording unit 200 to the subject or connects recording unit 200 to a docking station.

Figure 3:
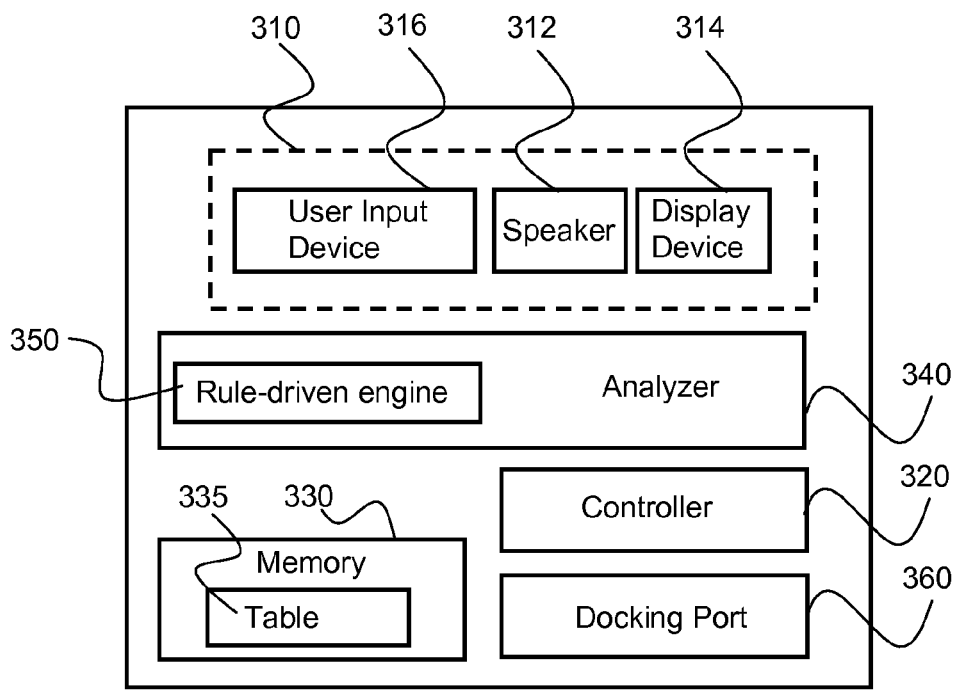
FIG. 3 is a block diagram of a docking station according to an example embodiment.

FIG. 3 is a block diagram of a docking station 300 according to example embodiment. FIG. 3 will be described in association with FIG. 2. Docking station 300 includes a user interface 310, a controller 320, a memory 330, an analyzer 340, and a docking port 360. User interface 310 may include a speaker 312, a display device 314, and a user input device 316. User interface 310 enables a user to provide user input to controller 320 regarding recording plan and related recording instructions that should be applied, ignored, substituted, or removed. Responsive to entering a corresponding user input by using user input device 316, controller 320 may output displayable and/or audible information to the user of docking station 300 regarding recorded signals, recording plan(s), specific recording instruction(s), and so on.

Docking port 360 enables communication with recording controller 220 of FIG. 3. During communication, recording controller 220 transfers recorded signals to controller 320. Controller 320, then, stores the recorded signals in memory 330 and instructs analyzer 340 to commence an analysis session to analyze the recorded signals. Analyzer 340 may use predefined signal patterns and/or predetermined criteria to identify irregularities or abnormalities in the recorded signals. The predefined signal patterns, predetermined criteria, metadata and information that associate events/scenarios with a recording plan, and data representing the predefined signal patterns may be held in memory 330, for example in table 335.

Some of the events/scenarios may be associated with the same recording plan. Analyzer 340 includes a rule-driven engine 350 that uses the data/information stored in the table in the way described below. If, after analyzing the recorded signals, analyzer 340 finds a potentially alarming event/scenario, rule-driven engine 350 uses the results of the signals' analysis to search in the table for a corresponding (i.e., like or similar) pre-stored event/scenario. If rule-driven engine 350 finds a corresponding event/scenario in table 335 rule-driven engine 350 searches in the table for a recording plan that is associated with the event/scenario. Upon finding the associated recording plan rule-driven engine 350 forwards the associated recording plan to controller 320. Controller 320 may, then, transfer the recording plan to recording controller 220 of recording unit 200 (i.e., the wearable recording unit that provided the recorded signals). The functionality of analyzer 340 is described in more detail below, in connection with FIG. 4.

Docking port 360 may be configured or adapted to physically and electrically engage with communication interface 260 of recording unit 200. If recording unit 200 has an electrical connector of a first type, docking port 360 includes, or is designed as, an electrical connector of a second type that matches the electrical connector of the first type. For example, recording unit 200 and docking station 300 may communicate via a USB interface. In order to enable USB communication the wrist strap (an example attachment device) of recording unit 200 includes a USB male connector and docking port 300 includes a matching USB socket.

Controller 320 may transfer to display device 314 various displayable data such as historical recording plans/instructions, current recording plans/instructions, and related metadata such as pertinent time stamps, etc. The user may use user input device 310 to instruct controller 320 to display on display device 314 any displayable information that is temporarily or permanently held, for example, in memory 330. The user may also use user input device 310 to alter a recording instruction, to delete a recording instruction, or to add a new recording instruction. The user may use speaker 312 to selectively playback audible recordings.

A recording instruction generated by controller 320 may be contingent on various factors such as historical events associated with the monitored subject, events that are expected to occur in view of historical events or regardless of such events, a user input, and so on. If, for example, the mother of a child expects that her babysitter will take her child to a nearby park tomorrow between 10:00 AM and 12:00 AM the mother may use user input device 316 to transfer a recording instruction to recording unit 200 to record the child's temperature and the ultra-violet radiation to which her child will be exposed tomorrow between, say, 9:30 AM and 12:30 AM. Such a recording may be executed with or without using a temperature threshold value. That is, if no temperature threshold value is to be used, recording unit 200 will record the child's temperature regardless of the temperature's values. Optionally, the mother may set a temperature threshold value and recording unit 200 will record between the specified times (i.e., between 9:30 AM and 12:30 AM) only temperatures whose values are higher than the set threshold value. Regarding the example described above, the child's mother may also transfer an instruction to recording unit 200 not to record environmental sounds between 10:00 AM and 12:00 AM because the park is known to be very noisy during that period.

Controller 320 may instruct recording unit 200 (i.e., instruct recording controller 220) to record a signal of a particular signal sensor (e.g., signal of signal sensor S2) responsive to the signal of the particular signal sensor, alone or in conjunction with signals of other signal sensors, matching a predefined pattern, or responsive to the value or average value of the sensor's signal exceeding a predetermined threshold value, or responsive to the value of the sensor's signal exceeding a predetermined value for a predetermined duration, or responsive to the spectral content of one or more of the signals matching predefined spectral content. The predefined pattern may indicate an abnormal condition of the subject or of the subject's environment which can trigger an alert.

For example, if the temperature of a monitored infant increases it is likely that the infant will start crying shortly afterwards. Should this event/scenario occur, the temperature signal monitored by recording unit 200 would present an abnormal temperature rise and, say, a few seconds later, an audio signal would have an abnormal pattern that represents the infant's cry. Therefore, temporal proximity of the two abnormal signals may indicate a problematic condition that the subject experienced, which is worth scrutinizing. A pattern may be abnormal in the time domain, in the frequency domain, or in both domains.

An instruction issued by controller 320 to recording unit 200, therefore, can instruct recording unit 200 to record the temperature signal and the audio signal if such scenarios occur. Two abnormal patterns of interest may originate from different sensors, as discussed above, or from the same sensor, as discussed below. For example, if a child is slammed on his/her face it is likely that the child will cry shortly after s/he is slammed or a few seconds later. Under such circumstances, a microphone of recording unit 200 would record the slam noise and concurrently, or a few seconds later, the child's cry.

Recording controller 220 of recording unit 200 may time stamp selected recordings to facilitate logging and retrieval of data/information, and extractions, by analyzer 340, of features from signals which are potentially alarming.

FIG. 4 is a block diagram of analyzer 340 of FIG. 3 according to an example embodiment. FIG. 4 will be described in association with FIG. 3. Analyzer 340 includes an audio interpreter 410; a temperature interpreter 420; an acceleration interpreter 430; a data integrator and rule-driven engine 440; and an archive data compressor 446.

As explained above in connection with FIG. 1, when recording unit 460 is in the docking mode it transfers one or more data files that represent the recorded signals to the docking station. Recording unit 460 may transfer (via docking port 360 and controller 320) the recorded signals to analyzer 340 as one data file that represents various types of recorded signals. Alternatively, recording unit 460 may transfer to analyzer 340 a data file for each type of signal, as demonstrated in FIG. 4. By way of example, recording unit 460 transfers to analyzer 340 an audio data file 470, a temperature data file 480, and an acceleration data file 490.

Audio analyzer 410 analyzes the data held in audio data file 470 in order to detect, or to identify, and classify audio patterns (i.e., audio events) as "normal" or as "exceptional" (i.e., abnormal). In the context of baby monitoring, an exceptional audio event is, for example, a burst of crying, a scream resulting from pain, a burst of laughter, etc. Such audio events can be detected by using algorithms that are known in the art of digital signal processing ("DSP"). For example, "An Acoustic Abnormal Detection System" (by Hideyuki MASUBUCHI and Hisato KOBAYASHI, Dept. of Electrical Eng., Hosei University, IEEE International Workshop on Robot and Human Communication) discusses a technique for detecting screams in audio signals. Other audio events in recorded audio signals, such as an audio signal representing distress or stress, can be evaluated by using DSP algorithms that have been developed by VoiceSense LTD, Israel.

Likewise, temperature interpreter 420 analyzes the data held in temperature data file 480 in order to detect, or to identify, exceptional temperature patterns (i.e., temperature events). By way of example, a "temperature event" can be an increase of environmental temperature to 45 degrees centigrade that follows the sound of slamming a car's door. Such an event may indicate that a baby was left in a locked car unprotected from the sun. An acceleration interpreter 430 analyzes the data held in acceleration data file 490 in order to detect/identify abnormal acceleration patterns (i.e., acceleration events). By way of example, an acceleration event is an impact that is typical to a person falling to the ground, or an acceleration pattern that is typical to a seesawing motion.

Data integrator and rule-driven engine 440 evaluates the analysis results of audio interpreter 410, temperature interpreter 420 and acceleration interpreter 430, and compares the times at which the various events occurred in order to determine whether the events, or some of the events, can be associated with some common context. Various signals may be associated with a context individually or collectively. That is, a context may be associated with abnormality in a single signal of some type, or with abnormalities in several signals of different types.

A context logically "binds" a cause event and an effect event, which means that if one event (i.e., the "cause" event) causes or results in another event (i.e., the "effect" event), the two events belong to, are associated with, or define a common context. By way of example, the following two events belong to the common context "an infant was left in a car unprotected from the sun": an audio event representing a slam of a car's door (i.e., a "cause" event) followed by a linear increase in temperature (i.e., an "effect" event. Other examples are: an impact followed by cry of pain (the context being an infant being slammed), repetitive motion at a typical rate of a crawling baby followed by a sudden increase in environmental temperature (the context being the baby crawled out of the house), etc.

If a pre-stored context is found for the identified/detected events, the rule-driven engine part of data integrator and rule-driven engine 440 searches in table 335 for recording rules that correspond to the found pre-stored context and that can be used to enhance the next recording session. If the rule-driven engine finds one or more recording rules, data integrator and rule-driven engine 440 uses the found one or more recording rules to adapt the recording plan for recording unit 460 (the adapted recording plan is shown at 442). Then, data integrator and rule-driven engine 440 may send adapted recording plan 442 to recording unit 460 via controller 320 and docking port 360, thus completing a virtual control loop for recording unit 460. By "control loop" is meant that signals recorded by recording unit 460 affect the way recording unit 460 records new signals during the next recording session. The control loop is "virtual" in the sense that the analysis of the recorded signals and the adaptation of the recording plan are done by an external apparatus (e.g., by the docking station). If more powerful and more miniaturized computing resources will be devised in the future, it is likely that the recording unit may also be able to assume at least some of the functionality of the docking station, for example the signal analysis and the adaptation of the recording plan.

Archive data compressor 446 compresses the data pertaining to recording plans, to recording instructions, and to alarm messages before storing it in data archive 450. Data archive 450 may be held in a remote system, and data may be transferred to/from data archive 450 over a data network. Data integrator and rule-driven engine 440 may use archived data to devise new recording rules. Data integrator and rule-driven engine 440 may send archived data to speaker 312 and/or to display device 314 responsive, for example, to a corresponding user input, or as a default option. Analyzer 340 may also include an alert messenger 444 for outputting alarm messages 448 to speaker 312 and/or to display device 314, and/or to a remote system.

Signals can be recorded using any recording quality (which is measured in bits per sample and in samples per second) that is provided by the recording unit. However, the highest the recording quality the more storage space the recording process requires. Therefore, recording signals only at the highest quality available requires a very large storage space, and lacking sufficient storage space will result in the recording sessions being very short. In order to reduce the size of the storage space and still enable long recording sessions, a mute mechanism can be used to allow recording a signal only if some parameter (e.g., the magnitude of the signal or a frequency thereof) satisfies a predefined criterion (e.g., the magnitude of the signal exceeds a predefined threshold value). Regardless of the criterion, there may be a need to start using a higher recording quality before an event occurs in order to "capture" the event while it is occurring. For example, if previously recorded signals show that a baby was crying without a reason at 12:10, the docking station may be configured to send a recording instruction to the recording unit to use a higher recording sensitivity, resolution and sampling rate, say, between at 12:00 and 12:20, to thereby provide more accurate data to analyzer 340.

Figure 5:
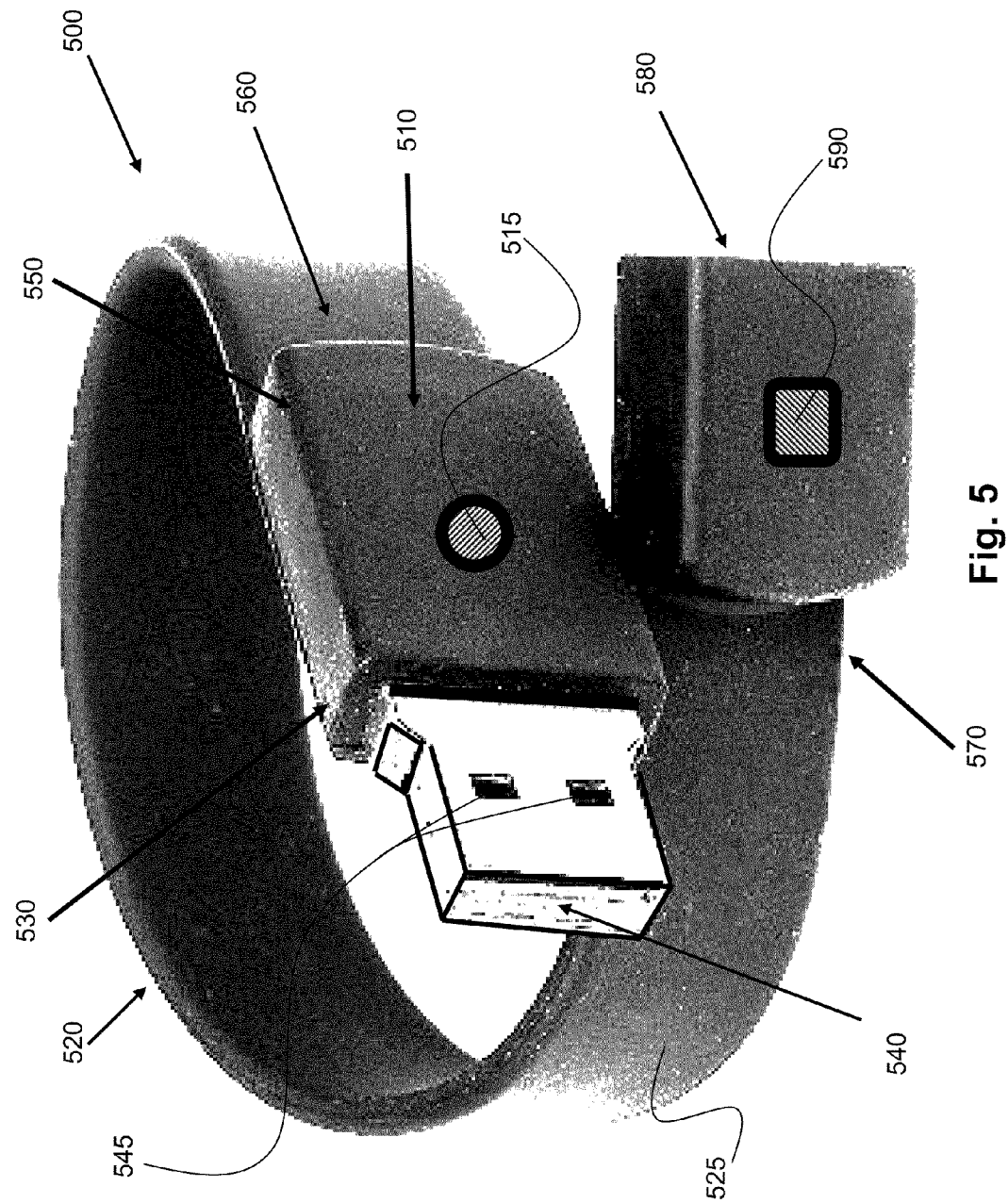
FIG. 5 depicts a wearable recording unit according to an example embodiment.

FIG. 5 depicts a wearable recording unit 500 according to example embodiment. Wearable recording unit 500 includes a recording unit 510 and a wrist strap 520, an exemplary attachment device, for attaching recording unit 510 to a monitored subject (not shown in FIG. 5). Wrist strap 520 may include a lock/unlock mechanism by which recording unit 510 may be tethered to a monitored subject. Recording unit 510 includes a microphone 515 and it may include other embedded sensors and/or sensors associated with it for sensing signals that pertain to the condition of the subject. Recording unit 510 may function in the same way as recording unit 200 of FIG. 2, or in a similar way.

Recording unit 510 has a first end 530 (referred to herein as a "connector end") that is affixed to a first electrical connector 540. A second end 550 of recording unit 510 (referred to herein as a "strap end") is affixed to a proximal end 560 of wrist strap 520. A distal end 570 of wrist strap 520 is affixed to, or it includes, a second connector 580. First electrical connector 540 and second electrical connector 580 are adapted to be functionally connected to a matching connector of a docking station. Electrical wires passing through a body 525 of wrist strap 520 electrically connect terminals of second connector 580 to recording unit 510. First electrical connector 540 may be, for example, a male USB connector and second electrical connector 580 may be, for example, a matching female USB connector.

First electrical connector 540 and second electrical connector 580 are provided with a locking mechanism: first electrical connector 540 is provided with recesses 545 and second electrical connector 580 is provided with a matching locking mechanism. Only a lock/unlock depressible button 590 of the matching locking mechanism is shown in FIG. 4.

Wearable recording unit 500 is attachable to the subject by using, for example, wrist strap 520 and by locking the two connectors (i.e., first and second connectors 540 and 580). While attached to the subject's hand, recording unit 510 may operate in the recording mode. In order to detach wearable recording unit 500 from the subject's hand the user of wearable recording unit 500 has to depress pushbutton 590 to unlock first connector 540 from second connector 580. After wearable recording unit 500 is detached from the subject's hand, recording unit 500 may transfer recorded signals to the docking station by engaging first connector 540 or second connector 580 with a matching connector of the docking station. Once wearable recording unit 500 is connected to the docking station, recorded signals can be transferred from recording unit 510 to the docking station, and, after the recorded signals are analyzed by the docking station, an updated or new recording plan can be transferred in the opposite way.

Because unplanned removals of wearable recording unit 500 are detectable by recording unit 510, there is no need to use a lock/unlock password to physically secure recording unit 500 to the monitored subject. Detecting an unplanned removal of wearable recording unit 500 from the subject may be done by checking, for example, whether the movement and/or audio signals imply that wearable recording unit 500 was removed without permission. That is, if, for some reason, no movement was recorded for a "considerable" amount of time, 'considerable' being dependent on the context (e.g., 15 minutes for one context and an hour for another context), it may be assumed that wearable recording unit 500 was removed from the subject. In addition, if the voice of the subject was not recorded for, say, 30 minutes, or it was recorded but it sounds faint, this may strengthen the impression (i.e., this may support the determination) that wearable recording unit 500 was removed. In another example, if no heartbeats were recorded for at least a certain period (e.g., several minutes), assuming the subject is alive this indicates that wearable recording unit 500 was removed. The capability of wearable recording unit 500 to identify its removal from a subject can, by itself, deter caregivers from tampering with wearable recording unit 500.

Figure 6:
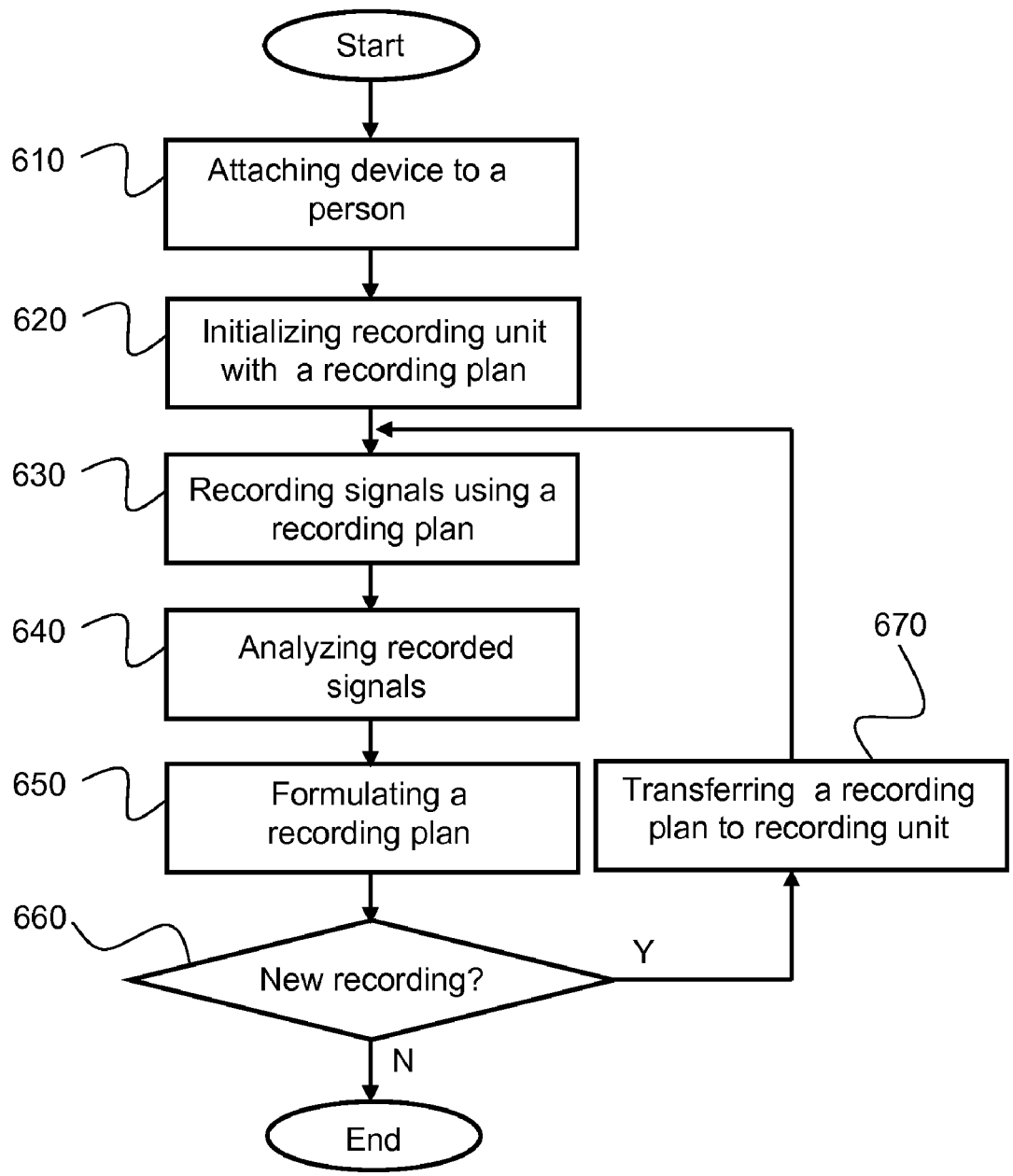
FIG. 6 is a method for monitoring a subject according to an example embodiment.

FIG. 6 is a method for monitoring a subject (e.g., an infant) according to an example embodiment. FIG. 6 will be described in association with FIGS. 1 and 2. At step 610 recording unit 200 is attached to a subject whose physiological condition is to be monitored and assessed. Recording unit 200 may be attached to the subject, for example, by using wrist strap 520 of FIG. 5, "hook-and-loop" fasteners (i.e., Velcro® fasteners), and the like.

At step 620 recording unit 200 is initialized with a default recording plan that includes a set of default recording instructions. The set of default recording plan may include one or more recording instructions. Recording unit 200 is initialized with a default recording plan because, lacking recorded signals when recording unit 200 is attached to a subject for the first time, recording controller 220 cannot generate recording instructions automatically (i.e., based on previously recorded signals) and, at this stage, there is no recording plan for controller 220 to update. Therefore, the first recording session is performed by using a default recording plan. By "recording session" is meant a single recording event in which recording unit 200 is in the recording mode. Detaching recording unit 200 from the monitored subject ends one recording session and reattaching recording unit 200 to the subject commences a new recording session.

At step 630 (while in the recording mode) recording unit 200 records sensors' signals according to the initial instructions that are specified by the initial recording plan. When a parent of the infant wants to review the recorded signals, or any portion or derivative thereof, the parent detaches recording unit 200 from the infant and connects it to docking station 300 of FIG. 3 for analysis.

At step 640 analyzer 340 of docking station 300 analyzes the recorded signals and at step 650 a new recording plan is formulated or devised by rule-driven engine 350 based on the analysis results, for example by finding in table 335 a corresponding recording plan, or by using pre-stored one or more rules to generate the corresponding recording plan. Formulating or devising a corresponding recording plan for the recording unit is referred to herein as "adapting the recording plan for the recording unit", or "adapting the recording plan" for short.

In general, generated recording plans and recording plans that are held in table 335 are used to enhance the signals recording process during the next recording session. Enhancing the signals recording process during the next recording session may include focusing on certain time periods during the day in which the infant seems to be mistreated, or focusing on certain signals during specific times. For example, an event/scenario may be an unusual cry of the infant to which controller 320 of docking station 300 may react by generating a recording instruction to sample the infant's environmental sounds for longer periods or more often. In other words, if the infant seems to cry more than s/he usually does, controller 320 may instruct recording controller 220 to record more samples the audio signal per unit of time or during the day. According to another example, if the infant was too quite controller 320 may sample the infant's temperature and heartbeat signals more often.

If a new recording session is to be commenced (shown as "Y" at step 660), controller 320 of docking station 300 transfers (at step 670) the corresponding recording plan to recording controller 220. That is, controller 320 of docking station 300 initializes recording unit 200 with a new or an updated recording plan.

Figure 7:
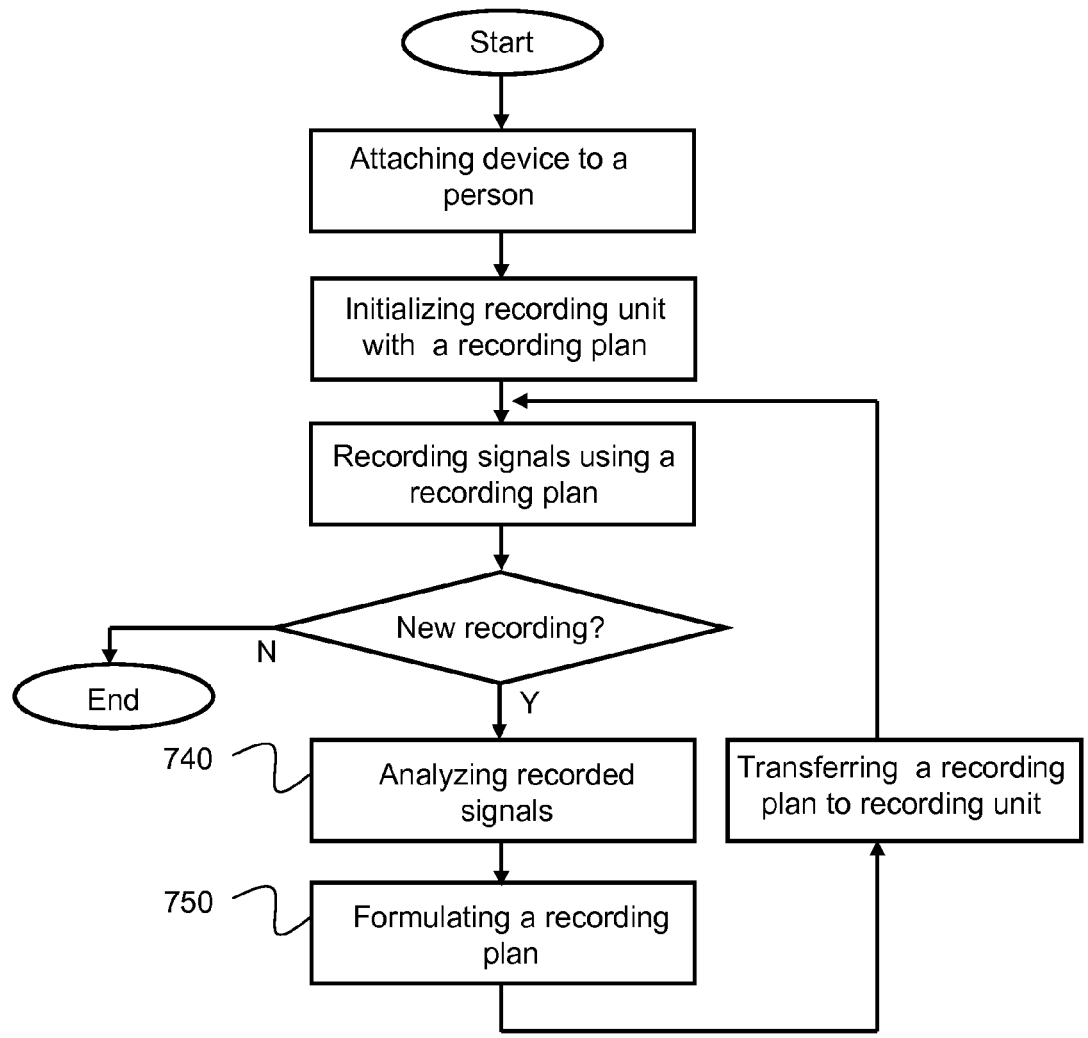
FIG. 7 is a method for monitoring a subject according to another example embodiment.

At step 630 recording controller 220 may use the new or updated (i.e., the adapted) recording plan to commence a new recording session. If recording unit 200 is not to be reattached to the infant (shown as "N" at step 660), no new recording session is commenced. Alternatively, analyzing recorded signals (i.e., step 640) and/or formulating/devising the recording plan (i.e., at step 650) may occur after a decision is made to reattach recording unit 200 to the infant, as shown in FIG. 7. Step 650 ("Formulating or devising a recording plan") may be implemented, for example, as shown in FIG. 8, which is described below.

FIG. 7 is a method for monitoring a subject according to another example embodiment. The method shown in FIG. 7 is identical to the method of FIG. 6 except that in FIG. 6 steps 640 and 650 are performed before a determination to commence a new recording session is made, whereas in FIG. 7 these steps (i.e., steps 740 and 750, respectively) are performed after the determination is made.

Figure 8:
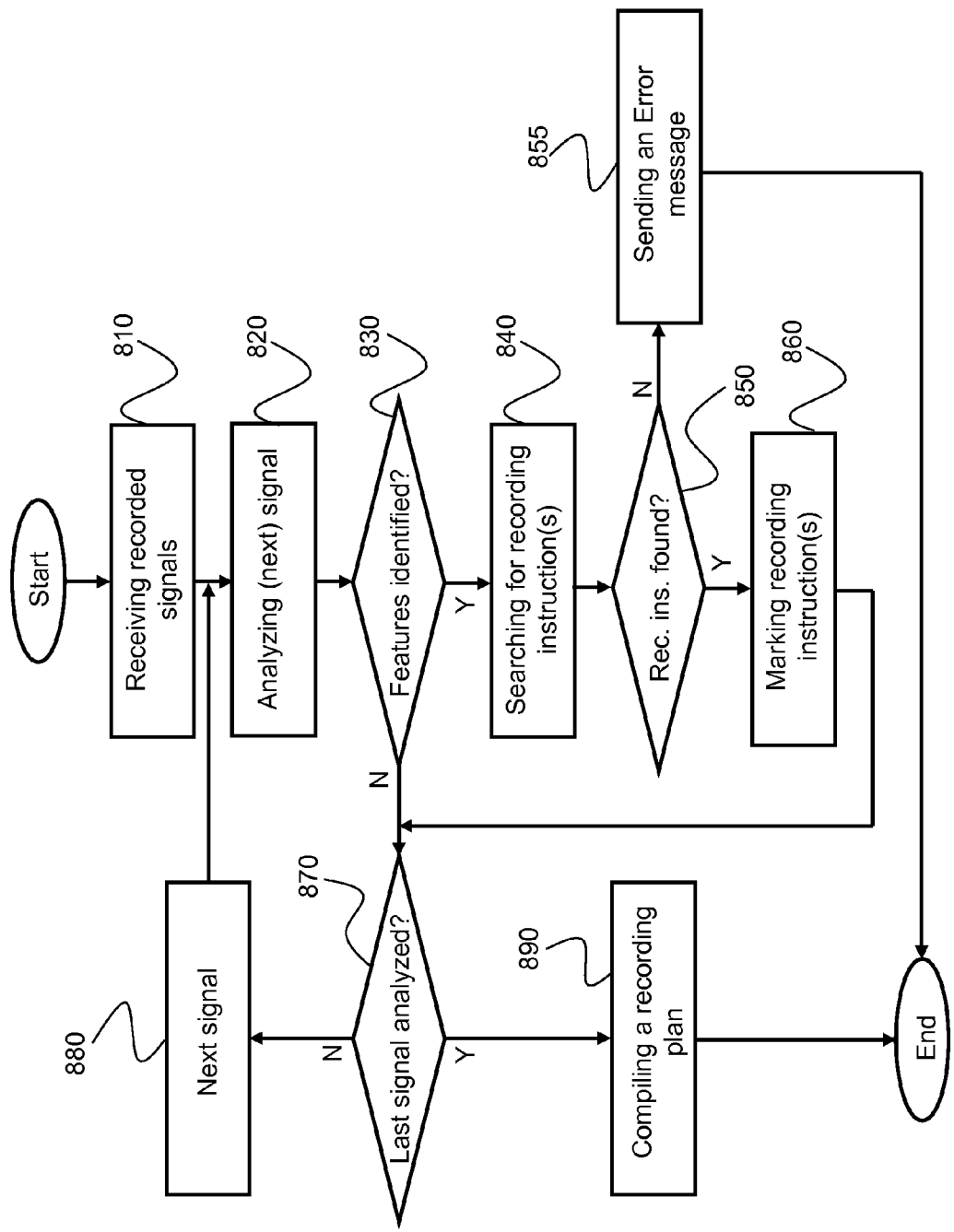
FIG. 8 is a method for compiling a recording plan according to an example embodiment.

FIG. 8 is a method for compiling a recording plan according to an example embodiment. FIG. 8 will be described in association with FIGS. 2 and 3. At step 810 docking station 300 receives signals (e.g., audio and temperature signals) that were recorded by recording unit 200. At step 820 docking station 300 analyzes a first recorded signal (e.g., the audio signal) in an attempt to identify in the analyzed signal abnormal patterns, irregularities, or features that may potentially indicate an alarming event (e.g., the monitored infant cried a lot when s/he was supposed to be sleeping). If such a pattern, irregularity, or feature is found in the analyzed signal (shown as "Y" at step 830), docking station 300 searches, at step 840, for a corresponding recording rule or rules. If a recording rule or rules is/are found (shown as "Y" at step 850), then, at step 860, the recording rule or rules is/are marked as "applicable" and/or temporarily stored in a memory, for example in memory 330 of docking station 300.

At step 870 it is checked whether there are other signals that need to be analyzed. If there is another unanalyzed signal (shown as "N" at step 870), the next signal (e.g., the temperature signal) is selected for analysis, at step 880. At step 820 the signal selected for analysis is analyzed by docking station 300 and steps 830 through 870 are repeated for each unanalyzed signal. After the last signal is analyzed (shown as "Y" at step 870), a recording plan is compiled, at step 890, from the temporarily marked or stored recording instructions. If recording unit 200 is functionally connected to docking station 300, docking station 300 may transfer the compiled recording plan to recording unit 200, as explained above. If no features are found in the recorded signals, then step 890 ("Compiling a recording plan") may include reverting to, or reusing, a basic or default recording plan.

If docking station 300 finds a problematic abnormal, irregularity, or feature in an analyzed signal (shown as "Y" at step 830) but it cannot find a recording instruction for that abnormality, irregularity, or feature (shown as "N" at step 850), then, at step 855 docking station 300 may issue an error message to the user of docking station 300 and/or to recording unit 200 and abort the recording plan generation process.

Figure 9:
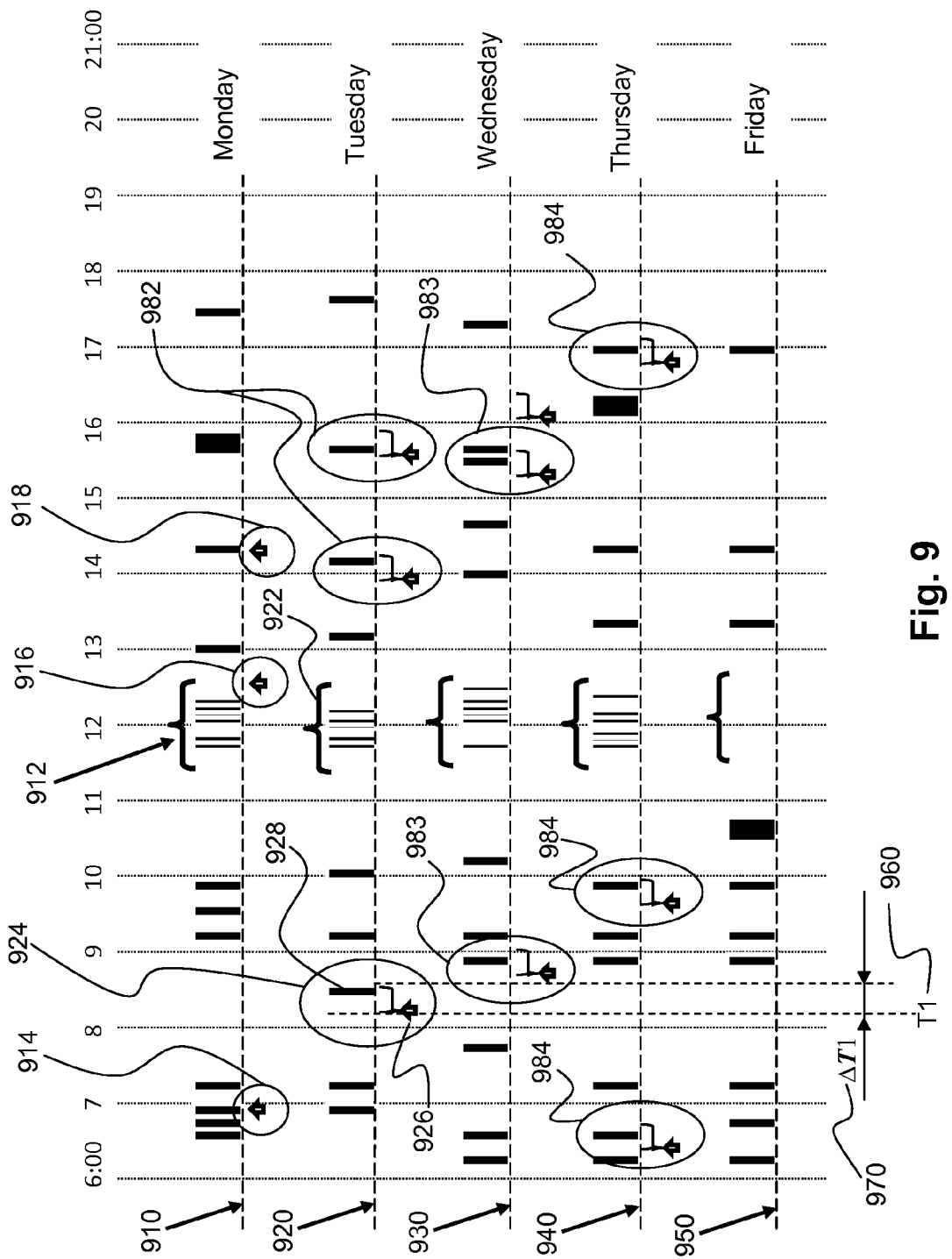
FIG. 9 is a daily-based event/scenarios diagram according to an example embodiment.

FIG. 9 is a daily-based event/scenario diagram according to an example embodiment. For simplicity, in this example it is assumed that: (1) a recording unit monitors a child using two sensors: a microphone and a movement detector, (2) the child was monitored five consecutive days between 6:00 AM and 9:00 PM, and (3) the recording unit uses a default recording plan that involves sampling signals at the lowest sampling rate (e.g., 8 kilohertz) and using the lowest resolution (e.g., 8 bits) available by the recording unit. The diagram, therefore, depicts five audio signal tracks (shown at 910, 920, 930, 940, and 950), each of which pertains to a different day. For example, audio signal track 910 pertains to Monday; audio signal track 920 pertains to Tuesday, etc.

In general, a recording plan may instruct a recording unit to use, for each recording session, one or more recording modes conditionally and one or more recording modes unconditionally. A recording instruction transferred from the docking station to the recording unit may instruct the recording unit to record signals using a basic recording mode that involves sampling one or more signals at the lowest sampling rate (e.g., 8 kilohertz) available by the recording unit, or using the lowest resolution (e.g., 8 bits per sample) available by the recording unit, or using both the lowest sampling rate and the lowest resolution. The recording unit may be instructed by the docking station to record signals using an enhanced recording mode that involves sampling one or more signals at a higher sampling rate (e.g., 16 kilohertz) and using a higher resolution (e.g., 16 bits per sample). Other recording modes may likewise be used. The higher the sampling rate and the higher the sampling resolution the more enhanced is the recording mode. The more enhanced is a recording mode the deeper the zoom-in level is at which a phenomenon in a signal can be analyzed. A docking station's instruction may, therefore, specify to a recording unit the signal or signals that should be recorded, the times at which the signal(s) should be recorded, and the recording mode at which the recording unit should operate when it records the specified signals at the specified times.

During a recording session the recording unit may initially operate at the basic operation mode and then it may change the recording modes while the recording session is ongoing and in compliance with the pertinent recording plan. In other words, a recording plan allows for using different recording modes during the same recording session.

By "using a recording mode unconditionally" is meant that the recording unit operates at a mode of operation irrespective of the signals that are recorded during the current recording session. The activation of unconditional modes depends solely on the analysis results of signals that were recorded in previous one or more recording sessions. By "using a recording mode conditionally" is meant that the recording unit operates at a specified mode of operation only responsive to a triggering event that is detected by the recording unit during the current recording session. Yet, the instruction to conditionally use a recording mode is derived from the analysis results of signals that were recorded in previous one or more recording sessions.

After the docking station analyzes the recorded signal pertaining to the first day (the recorded signal is shown at 910), the docking station identifies in signal 910 an abnormal crying pattern (shown at 912) of the child. Crying pattern 912 is regarded in this example as abnormal because the child was expected to be sleeping, say, between 11:30 AM and 12:30 PM. Therefore the docking station may determine (i.e., based on pre-stored recording-related rules) that if the child excessively cries between 11:00 and 13:00, then during the following one or more days the audio signal will be recorded using an enhanced recording mode. For example, the audio signal may be sampled using a slightly higher sampling rate (e.g., 10 kilohertz instead of 8 kilohertz) and a slightly higher resolution (e.g., 10 bits/sample instead of 8 bits/sample). Such a determination results in a first recording instruction that the docking station will send to the recording unit.

The docking station also identifies in the signal three points (shown at 914, 916, and 918) at which the child made a sudden movement. Because a sudden movement of a child may indicate a potentially alarming condition of the child or the child's environment, the docking station may determine (i.e., based on pre-stored recording-related rules) that if a sudden movement is detected in some day then during the following one or more days every time the recording unit detects a sudden movement the recording unit should immediately start operating at an enhanced operation mode for a specified time period. Such a determination results in a second recording instruction that the docking station will send to the recording unit. Because in this example the docking station could not identify or detect in signal 910 other meaningful phenomena, the docking station adapts the recording plan to the next recording session which is planned for Tuesday. The recording unit then uses the first and the second recording instructions that were derived from signal 910 to compile an updated recording plan. Using the first and the second recording instructions that were derived from signal 910 may be thought of as adapting the recording plan of the first recording session to the next recording session.

Signal 920 (i.e., the signal recorded on Tuesday) was recorded by using the two recording instructions that were derived from signal 910: (1) the first recording instruction that instructs the recording unit to use a more enhanced recording mode between 11:00 and 13:00, and (2) the second recording instruction that instructs the recording unit to use a more enhanced recording mode whenever the recording unit detects a sudden movement of the child. Referring to signal 920 by "more enhanced recording mode" is meant using a recording mode that is more enhanced than the recording mode used for recording signal 910.

Regarding using the first recording instruction to operate the recording unit at a more enhanced recording mode between 11:00 and 13:00, signal 920 contains a signal segment 922 that represents the cries of the child that were recorded by using the more enhanced recording mode specified by the first recording instruction. Regarding using the second recording instruction to operate the recording unit at a more enhanced recording whenever the recording unit detects a sudden movement of the child, signal 920 shows at 924 an event that was recorded by using the more enhanced recording mode. More specifically, is, until time T1 (shown at 960) the recording unit used some default basic recording mode. Then, while using the basic recording mode, a sudden movement 926 was detected by the recording unit at time T1, which, in accordance with the second recording instruction explained above, triggered the activation of a more enhanced recording mode for a time window ΔT1 (shown at 970) that was specified by the second recording instruction. Activation of the more enhanced recording mode for the time period ΔT1 allowed "capturing" the child cries (shown at 928) a few seconds later (i.e., after the sudden movement was detected). If the recording unit maintained the basic recording mode despite of the detected sudden movement 926, it is likely that the child cries 928 would have remained unrecorded and, therefore, unnoticed. After the time window (i.e., ΔT1) terminates the recoding unit may resume the basic recording mode or another recording mode, depending on the recording instructions that are derived from the analysis results of the previously recorded signal(s). The temporal width of ΔT1 may be measured in seconds or minutes. For example, ΔT1 may be set to 2 minutes. The docking station may change the value of ΔT1, for example, according to the intensity (i.e., according to the magnitude and/or the frequency) of recorded sudden movements. The intensity of sudden movements may be measured, for example, by analyzing their time characteristics, frequency characteristics, or both characteristics.

Additional two events 982 similar to event 924 were recorded on Tuesday between 14:00 and 16:00; two events 983 were recorded on Wednesday between around 9:00 and around 15:30; and three events 984 were recorded on Thursday between 6:00 and 7:00, around 10:00, and around 17:00. Events such as events 922 and 924 imply that the child was mistreated. Therefore, the reoccurrence of these events in the next days necessitates intervention of the child's parents because it seems that the child is subjected to some kind of abuse. After the problem is resolved, for example by warning the child's nanny or by employing another nanny, the recorded signal corresponding to Friday shows no reoccurrences of the events. That is, signal 950 shows no sudden movements and no incessantly cries between 11:00 and 13:00.

Analysis of recorded signals may be enhanced by including a speech analyzer in the docking station. For example, a speech analyzer may detect, through speech, psychological stress and different types of emotions. Techniques for detecting emotional states and stress through speech are discussed, for example, in U.S. Pat. Nos. 3,855,416; 3,855,417; 3,855,418; 3,971,034; 4,093,821 and 4,142,067, and in U.S. Patent Publication Nos. 2004/0249634 and 2005/0108775. Infants cry for different reasons that can be narrowed down to five simple cry types. That is, infants usually cry when they are hungry, bored, annoyed, sleepy, and/or stressed. An automatic cry analysis system is discussed, for example, in "Automatic Assessment of Infants' Levels-of-Distress from the Cry Signals" (by Qiaobing Xie, Rabab K. Ward, and Charles A. Laszlo, IEEE TRANSACTIONS ON SPEECH AND AUDIO PROCESSING, VOL. 4, NO. 4, July 1996). An infant's cry can be classified in the context of pain. A methodology for analyzing infants' cries in the context of pain is discussed, for example, in "A Bayesian Classifier for Baby's Cry in Pain and Non-Pain Contexts" (by H. E. Baeck and M. N. Souza, Proceedings of the 25th Annual International Conference of the IEEE EMBS, Cancun, Mexico, Sep. 17-21, 2003). Therefore, analysis of recorded signals may also be enhanced by a cry analyzer that can be incorporated, for example, into the docking station.

The articles "a" and "an" are used herein to refer to one or to more than one (i.e., to at least one) of the grammatical object of the article, depending on the context. By way of example, depending on the context, "an element" can mean one element or more than one element. The term "including" is used herein to mean, and is used interchangeably with, the phrase "including but not limited to". The terms "or" and "and" are used herein to mean, and are used interchangeably with, the term "and/or," unless context clearly indicates otherwise. The term "such as" is used herein to mean, and is used interchangeably, with the phrase "such as but not limited to".

Having thus described exemplary embodiments of the invention, it will be apparent to those skilled in the art that modifications of the disclosed embodiments will be within the scope of the invention. Alternative embodiments may, accordingly, include more modules, fewer modules and/or functionally equivalent modules.

What is claimed is:

1. A recording unit comprising:
one or more signal sensors for sensing signals pertaining to a condition of a subject;
a memory unit; and
a recording controller, wherein the recording controller is configured to:
execute a first recording instruction based on a recording plan to record first data received from the one or more signal sensors into the memory unit, wherein the first data includes first information received from a first sensor during a first time period and second information received from a second sensor during a second time period;
transfer the recorded first data from the memory unit to a docking station; and
execute a modified second recording instruction received from the docking station in response to transferring the recorded first data to the docking station, wherein the modified second recording instruction is adapted from a second recording instruction of the recording plan and wherein adapting is effected in response to an irregularity detected in the recorded first data;
wherein the irregularity in the recorded first data is detected at the docking station by:
recognizing a first abnormal pattern in the first information;
recognizing a second abnormal pattern in the second information; and
detecting a correlation between the first abnormal pattern and the second abnormal pattern.

2. The recording unit of claim 1, wherein the modified second recording instruction is operative to set a parameter associated with recording, wherein the parameter is associated with one of recording schedule, recording sensitivity, recording duration, and recording resolution.

3. A system comprising:
one or more signal sensors;
a recording unit operative to record one or more signals of the one or more signal sensors according to a recording plan; and
a docking station including:
an analyzer configured to analyze first data received from the recording unit and to produce an analysis based on the first data, wherein the first data is recorded according to the recording plan; and
a controller configured to:
adapt the recording plan to produce an adapted recording plan in response to an irregularity in the first data detected via the analysis, wherein the irregularity of the first data is detected by comparison of the first data to a predetermined pattern;
wherein the adapted recording plan uses enhanced sampling during a predetermined time frame in which a condition associated with the irregularity is likely to occur.

4. The system of claim 3, wherein the adapted recording plan is operative to determine one or more of schedule, sensitivity, duration, and resolution associated with recording of second data.

5. The system of claim 3, wherein the recording plan is adapted in response to one of:
the first data matching a predefined pattern;
an average value of the first data over a predetermined duration exceeding a first predetermined threshold value;
a value of the first data exceeding a second predetermined threshold value;
a time characteristic of the first data matching a predefined time characteristic; and
a frequency characteristic of the first data matching a predefined frequency characteristic.

6. The system of claim 5, wherein the predefined pattern is associated with an abnormal condition of a subject being monitored.

7. A method comprising:
recording first data according to a recording plan, wherein the first data includes first information received from a first sensor during a first time period and second information received from a second sensor during a second time period;
receiving a modified recording plan in response to detection of an irregularity in the first data, wherein the irregularity is detected by detecting a correlation between a first abnormal pattern recognized in the first information and a second abnormal pattern recognized in the second information, and wherein the modified recording plan is modified from the recording plan based on the irregularity; and
recording second data in accordance with the modified recording plan.

8. The system of claim 3, wherein the enhanced sampling includes sampling at a second sampling rate that is greater than a first sampling rate associated with the first data.

9. The system of claim 3, wherein the enhanced sampling includes sampling at a second resolution that is greater than a first resolution associated with the first data.

10. The system of claim 3, wherein the modified recording plan is determined by:
comparing the first data to table entries including one or more predetermined patterns, each table entry associated with a corresponding replacement recording plan;
detecting a match of the first data with one of the predetermined patterns; and
selecting the corresponding replacement recording plan as the modified recording plan.

11. The system of claim 10, wherein the predetermined patterns include at least one of a predefined signal pattern, a predetermined criterion, and metadata.

12. The system of claim 3, wherein the first data includes first information received from a first sensor during a first time period and second information received from a second sensor during a second time period, and wherein the analysis includes detecting the irregularity in the first data by:
recognizing a first abnormal pattern in the first information;
recognizing a second abnormal pattern in the second information; and detecting a correlation between the first abnormal pattern and the second abnormal pattern.

13. An apparatus comprising:
a controller; and
a non-volatile memory configured to:
   store first data received from the controller, the first data collected by the controller while executing a recording plan;
   provide the stored first data to a docking station; and
   store second data received from the controller, the second data resulting from the controller executing a modified recording plan received from the docking station, wherein the modified recording plan is modified from the recording plan based on the first data;
   wherein the modified recording plan is adaptively updated from the recording plan in response to detection of an irregularity of the first data with respect to a predetermined pattern; and
   wherein the modified recording plan uses enhanced sampling during a predetermined time frame.

14. The apparatus of claim 13, wherein the predetermined time frame is selected based on a likelihood of occurrence of a condition associated with the irregularity.

15. The apparatus of claim 13, wherein the enhanced sampling is associated with a second sampling rate that is greater than a first sampling rate associated with recording of the first data.

16. The apparatus of claim 13, wherein the enhanced sampling uses a second data collection resolution that is greater than a first data collection resolution associated with the first data.

17. The method of claim 7, wherein the modified recording plan is operative to set a parameter associated with recording, wherein the parameter is associated with a recording schedule.

18. The method of claim 7, wherein the modified recording plan is operative to set a parameter associated with recording, wherein the parameter is associated with a recording sensitivity.

19. The method of claim 7, wherein the modified recording plan is operative to set a parameter associated with recording, wherein the parameter is associated with a recording resolution.

20. The apparatus of claim 13, wherein the modified recording plan is operative to set a parameter associated with recording, wherein the parameter is associated with a recording schedule.

21. The apparatus of claim 13, wherein the modified recording plan is operative to set a parameter associated with recording, wherein the parameter is associated with a recording sensitivity.

22. The apparatus of claim 13, wherein the modified recording plan is operative to set a parameter associated with recording, wherein the parameter is associated with a recording duration.

23. The apparatus of claim 13, wherein the modified recording plan is operative to set a parameter associated with recording, wherein the parameter is associated with a recording resolution.

* * * * *